United States Patent [19]

Turchin

[11] Patent Number: 5,746,761
[45] Date of Patent: May 5, 1998

[54] DISPOSABLE LANCET FOR FINGER/HEEL STICK

[75] Inventor: Arkadiy Turchin, 278 Grove St., Apt. 7, Newton, Mass. 02166

[73] Assignee: Arkadiy Turchin, Newton, Mass.

[21] Appl. No.: 887,782

[22] Filed: Jul. 3, 1997

[51] Int. Cl.⁶ .................................. A61B 17/32
[52] U.S. Cl. .................................. 606/181
[58] Field of Search ..................... 606/181–183, 606/184, 185; 128/770

[56] References Cited

U.S. PATENT DOCUMENTS

| | | |
|---|---|---|
| 4,503,856 | 3/1985 | Cornell. |
| 4,738,261 | 4/1988 | Enstrom. |
| 5,100,427 | 3/1992 | Crossman. |
| 5,133,730 | 7/1992 | Biro. |
| 5,196,025 | 3/1993 | Ranalletta. |
| 5,267,963 | 12/1993 | Bachynsky .......... 606/182 |
| 5,314,441 | 5/1994 | Cusack et al. ........ 606/182 |
| 5,318,584 | 6/1994 | Lange. |
| 5,545,174 | 8/1996 | Schenk. |

Primary Examiner—Michael Buiz
Assistant Examiner—William W. Lewis

[57] ABSTRACT

A lancet type device (20) having a movable and retractable lancet (46) is disclosed. A lancet (46) beyond the end of a lancet body (24). The device includes an actuating, a retracting and locking mechanisms that move and retract a sharp distal tip (48) linearly into and out of contact with a patient's skin. The actuating mechanism includes an arm (26) with a blind conical hole (56) and a conical top (52) of a lancet body (24). The retracting and locking mechanism includes a blind cylindrical hole (58) of an arm (26), a cylindrical head (50) of a lancet body (24) and a spring (54). In one embodiment, a spring (54) is molded as a part of a lancet body (24). In another embodiment, a spring (68) is made as separate part from metal. Contact between a blind conical hole (56) and a conical top (52) moves a lancet body (24) in a linear direction along the axis. Contact between a cylindrical head (50) and a blind cylindrical hole (56) locks an arm (26) inside a case (22).

2 Claims, 4 Drawing Sheets

DISPOSABLE LANCET FOR FINGER/HEEL STICK

BACKGROUND

1. Field of Invention

The invention relates to a device for producing a drop of blood for blood sampling, and more particularly to such a device for moving and retracting a sharp lancet point to prick a patient's skin to produce a drop of blood.

1. Description of Prior Art

Lancets are used to pierce the skin of a patient, usually through the finger or through the heel for new-born children. Blood then flows through the incision where it is collected for testing in a blood collection tube such as a capillary tube or pipette.

Historically, early lancets generally had a handle and a sharp lancet tip extending therefrom. However, numerous problems are inherent with such lancets such as controlling the depth and angle of penetration by the lancet tip, controlling the force of the insertion, and the psychological affect to the user of seeing the exposed lancet tip.

The concern over possible cuts or nicks has become especially acute since the appearance of human immune deficiency virus (HIV) as well as other virus such as the Hepatitis B virus (HBV).

One attempt to avoid these and other problems with this early type of lancet was to create lancets having lancet tips that are spring loaded or having actuating mechanism includes an arm with a substantially "V" shaped groove to be injected into and removed from the patient's skin. Typically, these devices hide the lancet tip both before and after the incision is made to prevent its view by the patient, to minimize trauma to patient and to prevent inadvertent contact with the lancet.

Several types of such a lancet injector have been proposed—for example, in U.S. Pat. No. 5,545,174 to Schenk et al. (Aug. 13, 1996), U.S. Pat. No. 5,196,025 to Ranalletta et al. (Mar. 23, 1993) and U.S. Pat. No. 5,318,584 to Lange et al. (Jun. 7, 1994).

Above-mentioned lancet injectors have several disadvantages:

(a) Lancets have complicated design and included many parts.
(b) The manufacture of those lancets requires complicated and expensive equipment for automated assembly.

OBJECTS AND ADVANTAGES

It is therefore an object of the invention to provide a device for producing a drop of blood from a patient that does not pose a significant threat of injury to the user or others before and after the device is in operation to produce the drop of blood.

It is another object of the invention to provide a device for producing a drop of blood from a patient with minimal trauma to the patient.

It is another object of the invention to provide a sterile device for producing a drop of blood from a patient.

It is another object of the invention to provide a sterile device that does not need to be separately packaged in order to maintain sterility of the lancet point.

It is another object of the invention to provide a device for producing a drop of blood from a patient by moving a sharp object into contact with a patient's skin where the sharp object is hidden from the patient's view before, during and after operation of the device to produce the drop of blood.

It is another object of the invention to provide a device for producing a drop of blood from a patient by moving a sharp object into contact with a patient's skin where the motive force to move the sharp object into contact with the patient's skin is provided by the pinching motion of the user's hand.

It is another object of the invention to provide a device for producing a drop of blood from a patient that is simple to use and inexpensive to manufacture that means it has such a design that allows fast automated assembly.

DRAWING FIGURES

In the drawings, closely related figures have the same number but different alphabetic suffixes.

Figure 1:
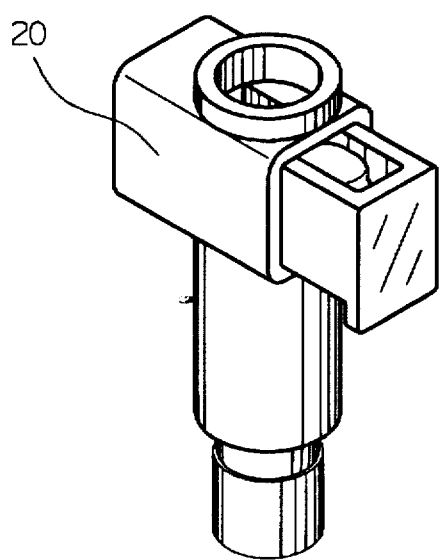
FIG. 1 shows a perspective view of fully assembled device in the "ready to use" position.

| Reference Numerals In Drawing | | | |
|---|---|---|---|
| 20 | generally labeled device | 22 | case |
| 24 | lancet body | 26 | arm |
| 28 | cap | 30 | patient contacting end |
| 32 | opposed proximal end | 34 | chamber |
| 36 | through hole | 38 | channel guide |
| 40 | cylinder | 42 | rod |
| 44 | tapered end | 46 | lancet |
| 48 | sharp distal tip | 50 | cylindrical head |
| 52 | conical top | 54 | spring |
| 56 | blind conical hole | 58 | blind cylindrical hole |
| 60 | slot | 62 | finger pad |
| 64 | alternate embodiment of lancet body | 66 | plug |
| 68 | metal spring | 70 | opposed end |
| 72 | peak of conical top | 74 | push-rod of assembly machine |

SUMMARY

In accordance with the present invention a lancet type device having movable and retractable lancet tip. The device includes an actuating, a retracting and locking mechanisms that move and retract the sharp distal lancet tip linearly into and out of contact with a patient's skin.

Description—FIGS. 1 to 11

Figure 2:
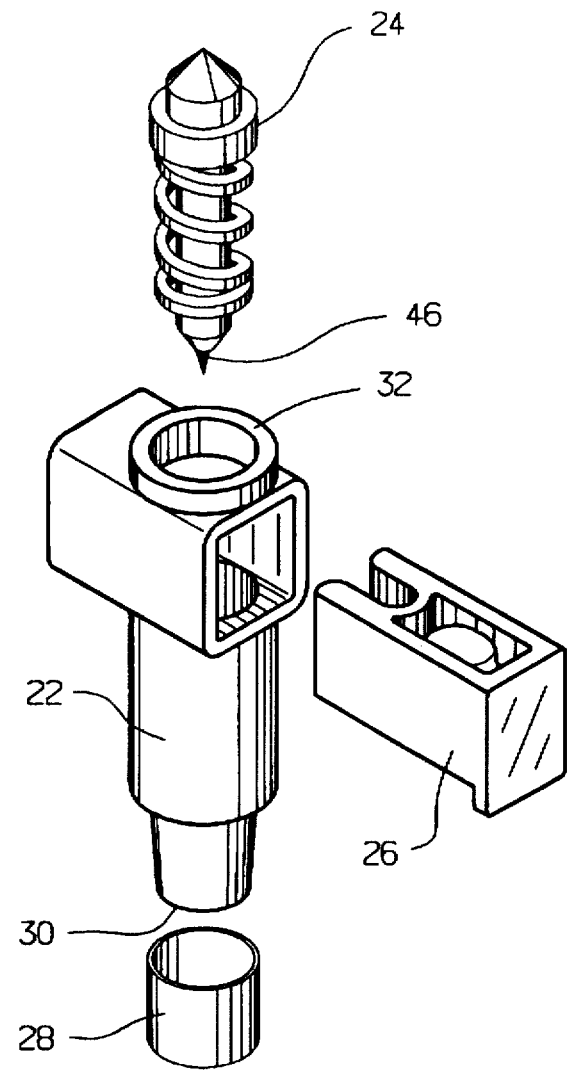
FIG. 2 shows exploded view of the device of FIG. 1.
Figure 3:
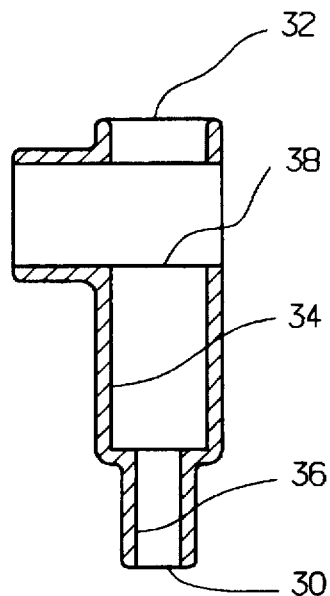
FIG. 3 shows a plan view of the case.
Figure 8:
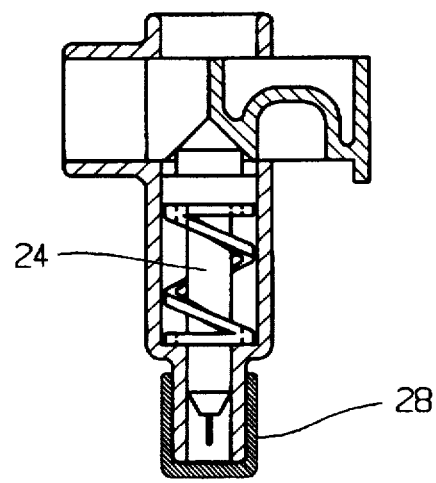
FIG. 8 shows a plan view with the lancet body and arm in position in the case with the cap covering the lancet tip in the "ready to use" position.
Figure 4:
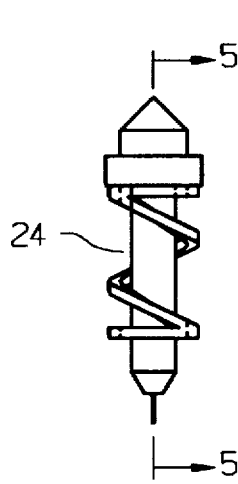
FIG. 4 shows a plan view of the lancet body of the preferred embodiment of the device.
Figure 5:
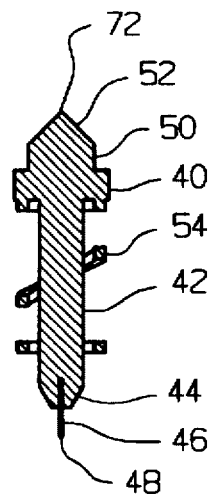
FIG. 5 shows a section view of the lancet body of FIG. 4.
Figure 6:
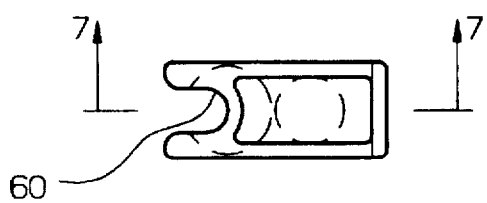
FIG. 6 shows top view of the arm.
Figure 7:
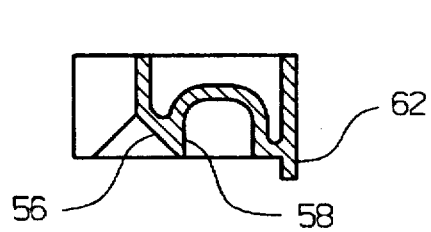
FIG. 7 shows section of the arm of FIG. 6.

A typical embodiment of a disposable lancet for finger/heel stick device is illustrated in FIG. 1 (perspective view of disposable lancet), FIG. 2 (exploded view), FIG. 3 (case), FIG. 4 and FIG. 5 (lancet body), FIG. 6 and FIG. 7 (arm), FIG. 8 (plan view).

A disposable lancet for finger/heel stick, generally labeled 20, has a case 22, a lancet body 24, an arm 26, and a cap 28 that covers a patient contacting end 30 to preserve the sterile condition of a lancet 46.

Case 22 has a chamber 34, a through hole 36, a transversal channel guide 38, an opposed proximal end 32, an opposed end 70. Lancet body 24 has a cylinder 40, a rod 42 with a tapered end 44, lancet 46 with a sharp distal tip 48, a cylindrical head 50, a conical top 52 with a peak of conical top 72, and a spring 54. The angle of conical top 52 is about ninety degrees. Spring 54 is molded from plastic as one part with lancet body 24.

Cylinder 40 has a diameter approximately the same as a diameter of chamber 34, rod 42 has a diameter approximately the same as a diameter of through hole 36 to provide sliding of lancet body 24 inside case 22.

Arm 26 has a blind conical hole 56, a blind cylindrical hole 58, a slot 60 and a finger pad 62. The width of slot 60 is approximately the same as a diameter of a push-rod 74, that is a part of the assembly machine (not shown).

The depth of blind cylindrical hole 58 is approximately the same as sum of heights of cylindrical head 50 and conical top 52 of lancet body 24.

As seen in FIG. 2 transversal channel guide 38 and profile of arm 26 have the same shape and approximately the same dimensions to provide sliding of arm 26 inside channel guide 38.

Figure 13:
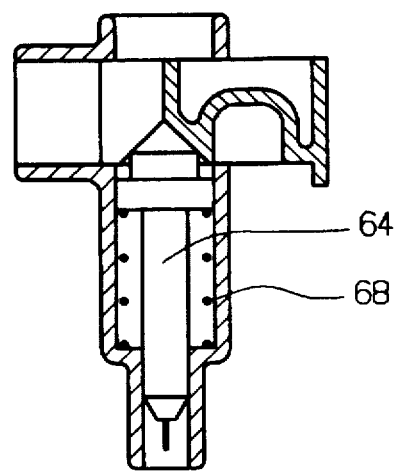
FIG. 13 shows alternate embodiment of the device with metal spring.

As seen in FIG. 13 disposable lancet of an alternate embodiment has a metal spring 68 and a lancet body 64 that molded without spring.

Figure 9:
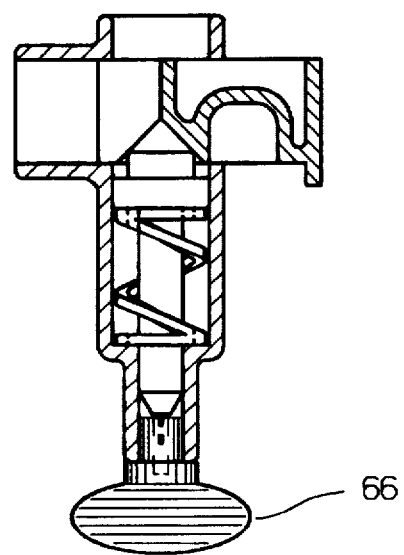
FIG. 9 shows a plan view with the lancet body and arm in position in the case with the plug covering the lancet tip of an alternate embodiment of the device.

As seen in FIG. 9 disposable lancet of an alternate embodiment has a plug 66 that covers a patient contacting end 30 to preserve the sterile condition of lancet 46.

Operation—FIGS. 10 TO 13, 14A TO 14D

Figure 10:
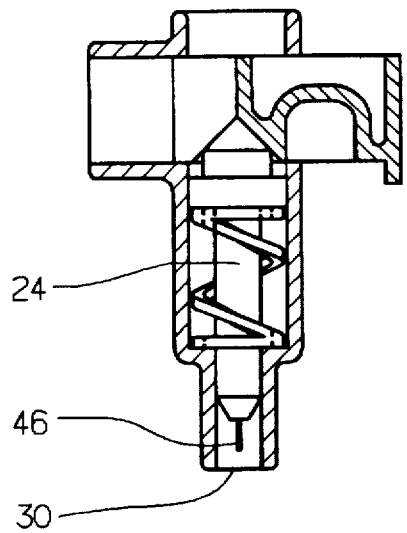
FIG. 10 shows a plan view of the device of FIG. 8 with the cap removed from covering the lancet tip.
Figure 11:
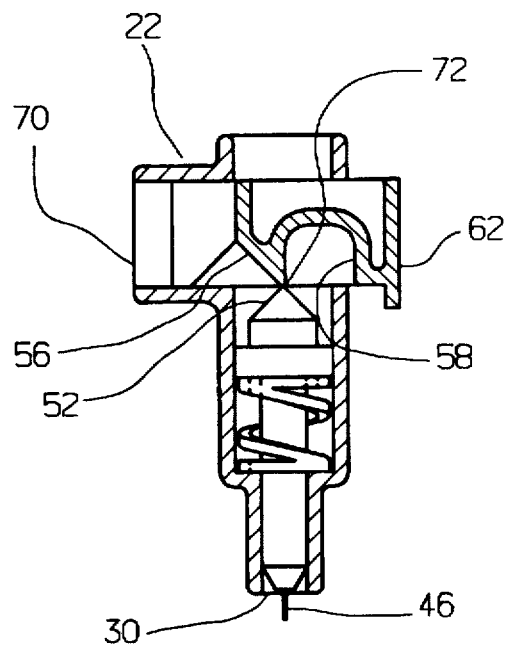
FIG. 11 shows a plan view of the device of FIG. 10 with the arm engaging the lancet body in the "lancet most distal" position.
Figure 12:
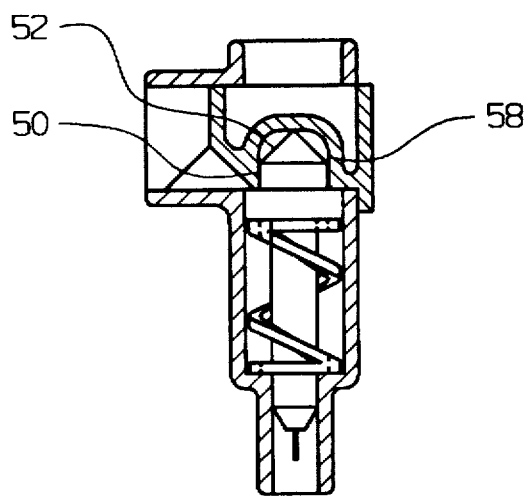
FIG. 12 shows a plan view of the device of FIG. 10 with the spring engaging the lancet body in the "used and locked" position.

FIGS. 10 to 12 show the operation of device 20. FIG. 10 shows device 20 in its "ready to use" position. In this position, device 20 may be transported and stored. To use device 20, cap 28 is removed. Because lancet body 24 is in its most proximal position, lancet 46 is not extended beyond patient contacting end 30. In this way, as shown in FIG. 10 the user may not come into contact with lancet 46 even with cap 28 removed.

To use device 20 to puncture the patient's skin, the user grasps device 20 between finger pad 62 and opposed end 70. The user then squeezes finger pad 62 toward case 22. Blind conical hole 56 of arm 26 forces conical top 52 and lancet body 24, distally.

Further movement of finger pad 62 causes arm 26 to move toward case 22 until lancet body 24 reaches the "lancet most distal" position, as shown in FIG. 11. In this position, peak 72 of conical top 52 of lancet body 24 is located between blind conical hole 56, and blind cylindrical hole 58 of arm 26. This causes lancet 46 to be moved to its most distal position. In this position, the geometry of device 20 is such that lancet 46 extends beyond the patient contacting end 30.

Further squeezing of finger pad 62 causes arm 26 to continue to move toward case 22 until the "used and locked" configuration shown in FIG. 12 is reached. During this operation, conical top 52 and cylindrical head 50 of lancet body 24 move into blind cylindrical hole 58 of arm 26. In the "used and locked" position, contact between cylindrical head 50 of lancet body 24, and blind cylindrical hole 58 of arm 26 locks device 20 with lancet body 24 in its most proximal position.

The act of squeezing finger pad 62 from the "ready to use" position shown in FIG. 10 to the "used and locked" position shown in FIG. 12 takes place in a rapid continuous motion. During this motion, lancet 46 punctures the patient's skin and then returns to "used and locked" position in a continuous rapid movement.

In an alternate embodiment, lancet body 64 is made without spring, and metal spring 68 is placed in case 22 before placement of lancet body 64, as shown in FIG. 13.

Figure 14A:
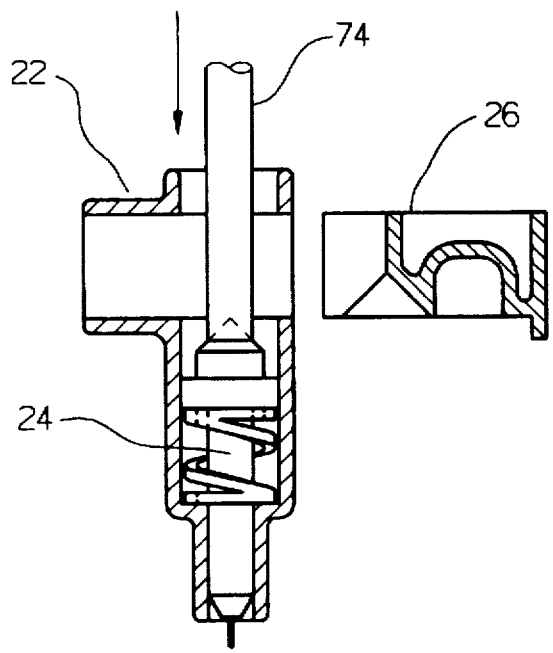
FIGS. 14A to 14D show sequence of assembly of the device.
Figure 14B:
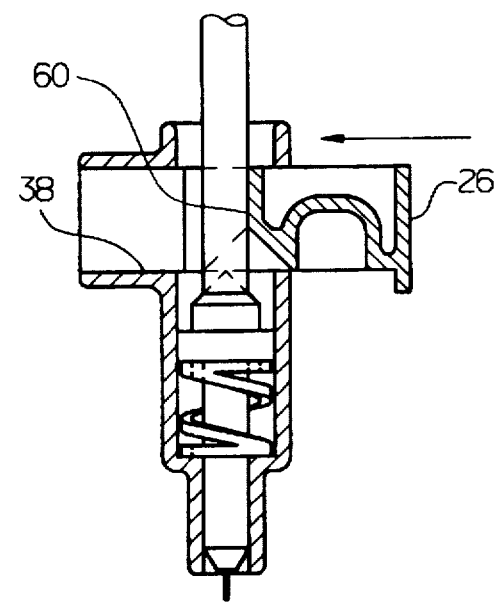
Figure 14C:
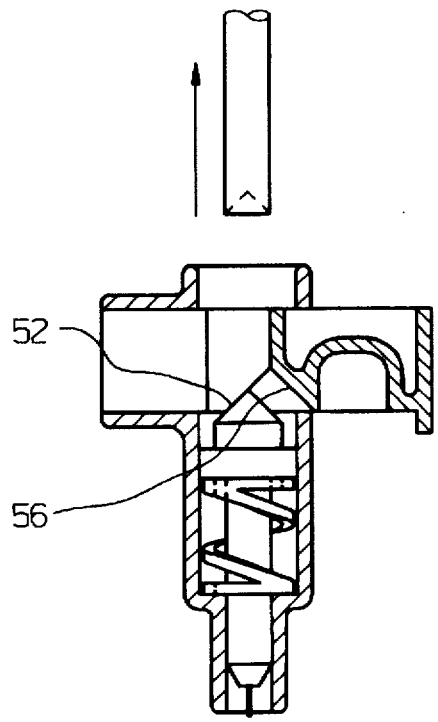
Figure 14D:
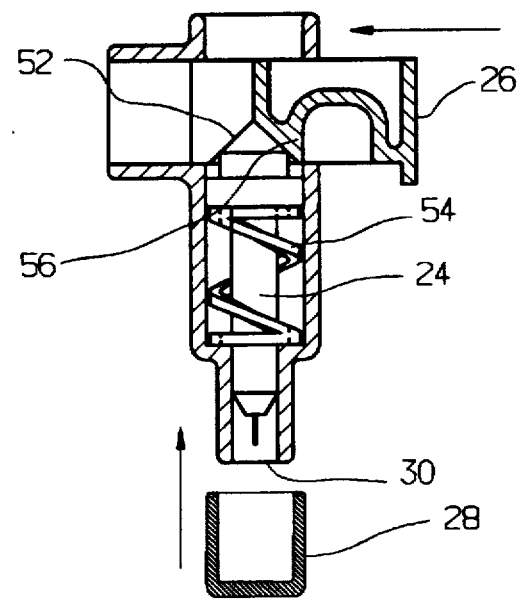

The method of assembly of device 20 shown in FIGS. 14A to 14D. To assemble device 20 lancet body 24 is placed in case 22, then push-rod 74, that is part of assembling machine, moves lancet body 24 to the "lancet most distal" position, as shown in FIG. 14A. Arm 26 is then placed in transversal channel guide 38 of case 22 to contact slot 60 to push-rod 74, as shown in FIG. 14B. Push-rod 74 is then retracted from case 22, and conical top 52 of lancet body 24 is contacted with blind conical hole 56 of arm 26, as shown in FIG. 14C. After that arm 26 is moved forward to place conical top 52 in blind conical hole 56. Lancet body 24 is engaged by spring 54 and locked arm 26 in this position, that is "ready to use" position until device 20 is to be used. To complete the assembly of device 20 cap 28 is placed on patient contacting end 30 of case 22. In alternate embodiment, to complete the assembly of device 20 plug 66 is placed on patient contacting end 30 of case 22.

SUMMARY, RAMIFICATIONS, AND SCOPE

Accordingly, the reader will see that the disposable lancet for finger/heel stick provides a device for producing a drop of blood from a patient that does not pose a significant threat of injury to the user of others before and after the device is in operation to produce the drop of blood.

. Furthermore, the disposable lancet for finger/heel stick has the additional advantages in that

- it provides a device for producing a drop of blood from a patient with minimal trauma to the patient;
- it provides a sterile device for producing a drop of blood from patient;
- it provides a sterile device that does not need to be separately packaged in order to maintain sterility of the lancet point;
- it provides a device for producing a drop of blood from a patient by moving a sharp object into contact with a patient's skin where the sharp object if hidden from the patient's view before, during and after operation of the device to produce the drop of blood;
- it provides a device for producing a drop of blood from a patient by moving a sharp object into contact with a patient's skin where the motive force to move the sharp object into contact with the patient's skin is provided by the pinching motion of the user's hand;
- it provides a device for producing a drop of blood from a patient that is simple to use an inexpensive to manufacture.

Although the description above contains many specificities, these should not be construed as limiting the scope of the invention but as merely providing illustrations of some of the presently preferred embodiments of this invention. For example, the finger pad can be slightly curved to allow the user's thumb to be more easily retained thereon, the cap can have other shape and a rough outer surface, to produce a high friction outer surface to prevent the user's fingers from sliding around the cap, the case can have other shape, the bottom of the blind cylindrical hole of the arm can be flat, spherical or conical, etc.

Thus the scope of the invention should be determined by the appended claims and their legal equivalents, rather than by the examples given.

I claim:

1. A lancet type device having a distal or patient contacting end and an opposed proximal end comprising:

an elongated lancet body having a central axis;

a lancet that is substantially encased in the lancet body, the lancet having a sharp distal tip that extends beyond the distal end of the lancet body;

an arm that sliding transverse to the axis of lancet body, the arm having opened slot on the front end, a blind conical hole, a blind cylindrical hole and a finger pad;

a case having a chamber contoured to the shape of the lancet body so that the lancet body is slidably encased in the chamber and moves in the chamber along the central axis of the lancet body, the chamber having an axis;

a case having a channel guide transversely across to the axis of lancet body, contoured to the shape of the arm so that the arm is slidably encased in the channel guide and moves in the channel guide transversely across to the axis of lancet body;

a removable cap that encloses the sharp distal tip;

an actuating mechanism that moves the sharp distal lancet tip linearly out of the case, the actuating mechanism including:
a conical top of lancet body
the blind conical hole of the arm;

a retracting and locking mechanism that moves the sharp distal lancet tip linearly into the case and locking the arm, the retracting and locking mechanism including:
a cylindrical head of the lancet body
a spring, that is molded as part of the lancet body
a blind cylindrical hole of the arm;

whereby, as the arm moves, contact between the blind conical hole of the arm and the conical top of the lancet body moves the lancet body in a linear direction along the axis of the lancet body;

whereby the lancet tip moves into and out of contact with a patient's skin.

2. A lancet type device having a distal or patient contacting end and an opposed proximal end comprising:

an elongated lancet body having a central axis;

a lancet that is substantially encased in the lancet body, the lancet having a sharp distal tip that extends beyond the distal end of the lancet body;

an arm that sliding transverse to the axis of lancet body, the arm having opened slot on the front end, a blind conical hole, a blind cylindrical hole and a finger pad;

a case having a chamber contoured to the shape of the lancet body so that the lancet body is slidably encased in the chamber and moves in the chamber along the central axis of the lancet body, the chamber having an axis;

a case having a channel guide transversely across to the axis of lancet body, contoured to the shape of the arm so that the arm is slidably encased in the channel guide and moves in the channel guide transversely across to the axis of lancet body;

a removable cap that encloses the sharp distal tip;

an actuating mechanism that moves the sharp distal lancet tip linearly out of the case, the actuating mechanism including:
a conical top of lancet body
the blind conical hole of the arm;

a retracting and locking mechanism that moves the sharp distal lancet tip linearly into the case and locking the arm, the retracting and locking mechanism including:
a cylindrical head of the lancet body
a metal spring
a blind cylindrical hole of the arm;

whereby, as the arm moves, contact between the blind conical hole of the arm and the conical top of the lancet body moves the lancet body in a linear direction along the axis of the lancet body;

whereby the lancet tip moves into and out of contact with a patient's skin.

* * * * *